United States Patent [19]

Irick, Sr. et al.

[11] Patent Number: 6,052,182
[45] Date of Patent: Apr. 18, 2000

[54] FIBER QUALITY MONITOR

[75] Inventors: Glenn E. Irick, Sr.; Luo Cheng; Youe-Tsyr Chu; Mark A. Overbay; Hossein M. Ghorashi; Michael E. Galyon, all of Knoxville; Gordon F. Williams, Norris, all of Tenn.

[73] Assignee: Zellweger Uster, Inc., N.C.

[21] Appl. No.: 08/962,973

[22] Filed: Oct. 28, 1997

[51] Int. Cl.$^7$ .................................................. D01G 15/46
[52] U.S. Cl. .......................................... 356/238; 356/245
[58] Field of Search ..................................... 356/385, 245, 356/376, 375, 73.1, 238, 242, 243; 250/237 G; 139/319; 73/160; 209/509, 511, 536, 576, 577, 580, 587, 524–526

[56] References Cited

U.S. PATENT DOCUMENTS

| | | | |
|---|---|---|---|
| 3,722,434 | 3/1973 | Strther et al. ............................ | 250/227 |
| 5,301,129 | 4/1994 | McKaughan et al. ................... | 356/430 |
| 5,319,445 | 6/1994 | Fitts ........................................ | 356/376 |
| 5,379,764 | 1/1995 | Barnes et al. ............................ | 356/39 |

OTHER PUBLICATIONS

Loptex, Optalyser OP 300 brochure, date unknown.
Schlichter, *Trutzschler nep tester NT: a new visual method to analyze neps and interfering particles*, Textile Praxis International, pp. 28–29, Sep., 1991.
Trutzschler, Nep Tester NT brochure, date unknown.
Lintronics, Fiber Contamination Tester brochure, date unknown.
Lieberman and Zhao, Categorizing Cotton Trash Shapes Using Video Imagery, Beltwide Cotton Conference, pp. 854–858, 1991.
Lieberman, Bragg, and Brennan, *Determining Gravimetric Bark Content in Cotton with Machine Vision*, Textile Res. J., pp. 94–104, Feb. 1998.
Zellweger Uster, Uster LVI brochure, date unknown.
Zellweger Uster, Uster Micronaire 775 brochure, date unknown.
Zellweger Uster, Uster HVI 900 brochure, date unknown.
Peyer, texLAB brochure, date unknown.
Peyer, FL–100 manual (2 pages only), date unknown.
Benardin, Delfosse, *Measurement of fiber lengths distribution on raw wool*, Melliand International, pp. 70–74, Feb., 1996.

(List continued on next page.)

*Primary Examiner*—Frank G. Font
*Assistant Examiner*—Tu T. Nguyen
*Attorney, Agent, or Firm*—Luedeka, Neely & Graham, PC

[57] ABSTRACT

A fiber quality monitoring apparatus is constructed with a sample window for viewing a fiber sample. As the fiber sample passes the sample window, a bulb is strobed to produce a light pulse that is directed toward and reflected by the fiber sample. When the light pulse reaches a desired intensity, a first photo diode generates a synchronization signal. A second photo diode detects reflected light with a wavelength between about 500 nanometers and about 600 nanometers and produces a reflection signal. A third photo diode detects reflected light with a wavelength between about 430 nanometers and about 530 nanometers and produces a color signal. A charge coupled device camera is positioned to receive the reflected light pulse. The charge coupled device camera has an array of pixels which receive the reflected light pulse. Pixels receiving the reflected light pulse at an intensity below a desired value are designated as dark pixels and pixels receiving the reflected light pulse at an intensity greater than the desired level are designated as light pixels. A prism focuses the reflected light pulse received by the second and third photo diodes, and a transparent block encloses the strobing Xenon bulb and the first photo diode so that the light pulse is conducted from the Xenon bulb to the first diode. Processing means analyze the color signal and the reflection signal and produce a composite value, and a percentage value representing the percentage of dark pixels in the array of dark and light pixels. Furthermore, the processing means recognizes and classifies patterns of dark pixels in the array of light and dark pixels, and controls fiber processing equipment in response to the composite and percentage values.

29 Claims, 2 Drawing Sheets

OTHER PUBLICATIONS

Motion Control, breaker drawings (2), Oct., 1994.

B. Xu, C. Fang, and M.D. Watson, Chromatic Image Analysis for Cotton Trash and Color Measurements, Cotton Quality Measurements Conference, pp. 532–540, 1997.

FIBER QUALITY MONITOR

FIELD OF THE INVENTION

The present invention is directed to a fiber quality monitoring device. More particularly the invention relates to a cotton quality monitor for detecting properties of cotton in an on-line or off-line mode.

BACKGROUND OF THE INVENTION

Cotton gins are used to separate cotton fiber from the seed and waste. Monitoring the properties of the cotton fiber passing through a gin to assure that the gin is functioning properly is important to obtaining a quality product. Historically, cotton has been classed according to, among other things, its color, leaf content, preparation, trash content, fiber length, micronaire and fiber strength. Originally, the classification of cotton relied upon the senses of human classers who would visually observe the cotton and assign it a grade accordingly. However, the use of human classers tends to be unreliable and heavily dependent upon the skill of the individual. In modern times, most cotton quality determinations are typically made by high-volume instruments. In order to monitor the desired properties of the cotton fiber, many conventional machines use an incandescent light bulb to illuminate the cotton as it rests upon a sample window from which it can viewed. The light that is reflected off of the cotton sample is then received by a photo sensitive detector. By examining the intensity of different wavelengths of light reflected by the sample, readings representing the quality and class of the cotton can be obtained.

Several disadvantages result from the use of an incandescent bulb to illuminate the cotton sample. Because the bulb is left on continuously when the gin is running, the intensity of the light produced by the bulb decays over time. Furthermore, in order to emit a white light of the desirable color temperature, an incandescent bulb must run at a high current. Continuous use of an incandescent bulb at a high current results in a dramatically reduced useful bulb life. Additional problems result from the vibration associated with cotton processing machinery. Like the degradation of the bulb over time, these vibrations affect the intensity of the light produced by the incandescent bulb, causing it to flicker. Thus, the intensity of the light reflected from the cotton sample tends to vary without variation in the quality of the cotton being observed. These vibrations also have a tendency to break the filament of the incandescent bulb. The net effect of using an incandescent bulb, that produces light of varying intensities, is that the sensors of the monitoring device must constantly be recalibrated and the incandescent bulb must frequently be replaced.

Another problem with traditional sensing methods is that, because of the relatively slow imaging speed of the photo sensitive detector, the speed of the cotton fiber passing in front of the constantly illuminated sample window tends to blur the image received by the photo sensitive detector. This tends to create an averaged, rather than an instantaneous reading. In order to receive a clear reflection for an instantaneous reading, the fiber moving through the processing machine must be stopped when the measurement is taken or a sample of fiber must be removed from the stream of fiber and placed upon the sample window.

What is needed, therefore, is a method and apparatus for measuring fiber properties that overcomes the problems of unreliability and inconsistency attendant with present fiber monitoring devices.

SUMMARY OF THE INVENTION

The present invention overcomes the above-mentioned problems by providing a fiber quality monitoring device with a sample window for viewing a fiber sample. A strobing light source provides a light pulse that is directed toward and reflected by the fiber sample. A first photo sensitive detector is positioned to receive the reflected light pulse and measure properties of the fiber sample. The present invention substantially diminishes the need for constant calibration and frequent bulb replacement by using a strobed light source. Additionally, the short pulse of light created by a properly strobed light source effectively freezes the reflected image of the fiber in front of the sample window, thus, reducing the need for a stationary fiber sample.

In one preferred embodiment of the present invention, a fiber quality monitoring apparatus is constructed with a sample window for viewing a fiber sample. As the fiber sample passes the sample window, a Xenon bulb is strobed to produce a light pulse that is directed toward and reflected by the fiber sample. When the light pulse reaches a desired intensity, a first photo diode generates a synchronization signal. The synchronization signal is generated on the negative edge of the light pulse. In synchronization with the synchronization signal, a second photo diode, that is positioned to receive the reflected light pulse, detects light with a wavelength between about 500 nanometers and about 600 nanometers and produces a reflection signal. A third photo diode, that is also positioned to receive the reflected light pulse in synchronization with the synchronization signal, detects light with a wavelength between about 430 nanometers and about 530 nanometers and produces a color signal.

A charge coupled device camera is also positioned to receive the reflected light pulse. The charge coupled device camera has an array of pixels which receive the reflected light pulse. Pixels receiving the reflected light pulse at an intensity below a desired value are designated as dark pixels and pixels receiving the reflected light pulse at an intensity greater than the desired level are designated as light pixels. A prism focuses the reflected light pulse received by the second and third photo diodes, and a transparent block encloses the strobing Xenon bulb and the first photo diode so that the light pulse is conducted from the Xenon bulb to the first diode.

Processing means analyze the color signal and the reflection signal and produce a composite value, and a percentage value representing the percentage of dark pixels in the array of dark and light pixels. Furthermore, the processing means recognizes and classifies patterns of dark pixels in the array of light and dark pixels, and controls fiber processing equipment in response to the composite and percentage values.

In the preferred embodiment, the fiber sample is placed on the sample window by a paddle which captures the fiber sample from a stream of air entrained fiber. The fiber sample may be a fiber batt sliding past the sample window or it may be air entrained fiber flowing past the sample window in a stream. The preferred embodiment allows the fiber to move rapidly past the sample window without the need to remove a sample for viewing.

A method of monitoring fiber quality includes viewing a fiber through a sample window. A light source is strobed to produced a light pulse that is directed toward and reflected by the fiber sample. The intensity of the reflected light pulse at a wavelength is detected and represents properties of the fiber sample.

In a preferred method, the fiber sample is viewed through a sample window. A Xenon bulb is strobed to produce a light pulse that is directed toward and reflected by the fiber sample. A synchronization signal is generated when the intensity of the generated light pulse reaches a desired level on the negative edge of the light pulse. The reflected light pulse is focused. A first intensity of the reflected light pulse at a wavelength between about 500 nanometers and about 600 is detected and a reflection signal based upon the first intensity is produced in synchronization with the synchronization signal. Likewise, a second intensity of the reflected light pulse at a wavelength between about 430 nanometers and about 530 nanometers is detected and a color signal based upon the second intensity is produced in synchronization with the synchronization signal. The reflected light pulse is also received by pixels. An array of light and dark pixels is created by designating each pixel receiving the reflected light pulse at an intensity below a desired value as a dark pixel and designating each pixel receiving the reflected light pulse at an intensity greater than the desired value as a light pixel.

The color signal and the reflection signal are analyzed to produce a composite value, and a percentage value is also produced, representing the percentage of dark pixels in the array of dark and light pixels. In addition, patterns of dark pixels in the array of light and dark pixels are recognized and classified. Fiber processing equipment is controlled in response to the composite and percentage values. In the preferred method, the fiber sample can be captured from a stream of air entrained fiber and placed on the sample window. The fiber sample may slide past the sample window in a batt of fiber, or flow past the sample window in a stream of air entrained fiber.

Strobing the light source allows measurements to be taken without stopping the flow of fiber in front of the sample window and allows all the measurements to be taken when the light is at a constant intensity. If the light source is left on continuously, the intensity of the light at the time the samples are taken is unknown and subject to variations due to vibration and decay. Thus, the aforementioned method of strobing the light source greatly diminishes the need for calibrating the sensing devices in response to changes in the intensity of the illuminating light. Furthermore, since the intensity of the light at the time the sample is taken is less than the intensity produced by a new bulb, the bulb is still useful after significant degradation in the maximum intensity of light produced.

BRIEF DESCRIPTION OF THE DRAWINGS

Further advantages of the invention will become apparent by reference to the detailed description of preferred embodiments when considered in conjunction with the following drawings, which are not to scale, in which like reference numerals denote like elements throughout the several views, and wherein.

DETAILED DESCRIPTION OF THE INVENTION

Figure 1:
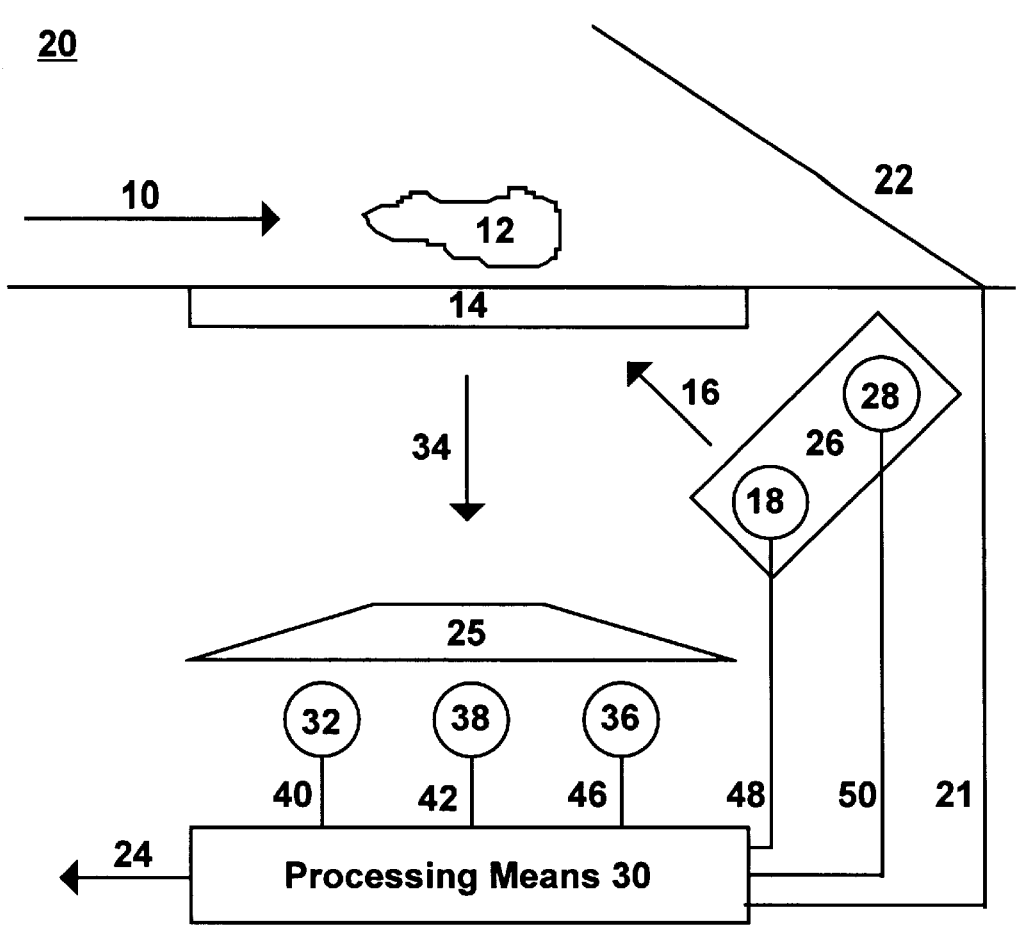
FIG. 1 is a functional diagram of an embodiment of the monitor.

Referring to FIG. 1, a monitor 20 is illustrated that includes the present invention. The monitor 20 is particularly useful for monitoring the quality and characteristics of cotton passing through a cotton gin. Alternately, the monitor 20 can monitor the quality of cotton in a mill. Either of these monitoring operations can be performed in an on-line mode, where the monitor 20 is attached to processing equipment, or in an off-line mode, where the monitor 20 is a separate piece of equipment that may be located in a laboratory. When used in an on-line mode, the monitor 20 may be a part of a control system that controls the operation of the equipment to which it is attached. For example, the monitor 20 may be used to measure the leaf content of the cotton fiber, variations in the cotton fiber color, or the presence of extraneous matter mixed in with the cotton fiber. This information may be used to control the cleaning operation in a gin. The construction of the monitor 20 is such that it could also be used to monitor the properties of other kinds of fiber as long as the properties that are desired to be measured can be determined by the character of the light that is reflected from the fiber as discussed below.

The monitor 20 monitors a fiber sample 12 and determines certain properties that the fiber sample 12 possesses. These properties are used to class the fiber sample 12. The basic idea is that certain properties of the fiber sample 12 can be determined by examining the light 34 reflected by the fiber sample 12. The fiber sample 12 is placed in front of a sample window 14. It will be appreciated that the fiber sample 12 can pass the sample window 14 of the monitor 20 in a variety of ways. The monitor 20 may be located on the bottom of a duct and the fiber sample 12 may slide past the sample window 14 in a batt, sliver, or mass of fiber. Alternatively, the fiber sample 12 may flow past the sample window 14 of the monitor 20 entrained in an air flow 10. The fiber sample 12 may also be captured from the air stream 10 and placed upon the sample window 14 by a device such as a paddle 22, which is connected to a processing means 30 by means of a line 21. Preferably, a sample window 14 having a size of about 3.5 inches by about 3.5 inches is used, although a larger window 14 can also be used. The sample window 14 is preferably formed of a material that is relatively transparent to certain wavelengths of light as described more completely below. For example, the sample window 14 may be formed of glass, quartz, sapphire, or appropriate thermoplastic resins, and is preferably formed of water clear PYREX.

Regardless of the method that is used to bring the fiber sample 12 to the monitor 20, when the fiber sample 12 passes the sample window 14, a bulb 18 is strobed to produce a light pulse 16. Only one bulb 18 is depicted in FIG. 1 for the sake of clarity. However, two bulbs 18 are used in the preferred embodiment, with the bulbs 18 set at opposite ends of the sample window 14, and disposed at 45 degree angles to the sample window 14. This arrangement provides a more uniform illumination of the fiber sample 12.

As discussed below, a Xenon bulb 18 is used in the preferred embodiment due to the desirable properties and characteristics of the bulb and the light produced by it. A preferred Xenon bulb is model number SFT4044T manufactured by Shokai Far East Ltd. of Peekskilly N.Y. The preferred bulb 18 has a maximum output of 45 joules at 300 volts. This gas bulb has a resistance of about 0.1 ohms when fired. Preferably, it is strobed with a voltage pulse of about 4 kilovolts to about 10 kilovolts having a pulse duration of about 1 microsecond. The lamp voltage can be adjusted from about 150 to about 300 volts, and the preferred voltage is about 175 volts.

A Xenon bulb tends to produce a white light which covers at least a portion of the visible spectrum and has a color temperature greater than about 6000 degrees Kelvin. In some applications, this amount of light is brighter than that which is desirable. If so, the intensity of the light that the bulb 18 produces may be diminished by placing a resistor in series with the bulb 18 or, more preferably, by varying the voltage of the bulb 18. The resistor also tends to increase the duration of the light pulse 16 that the bulb 18 produces.

In the preferred embodiment, the Xenon bulb 18 receives a voltage on signal line 48 from the processing means 30 that causes it to be strobed approximately every five to six seconds. However, the preferred embodiment is capable of strobing the bulb 18 at a considerably faster rate. The maximum flash and sample rate of the monitor 20 is largely determined by the driver used to flash the bulb 18. It should be noted that the invention is not limited to the use of a Xenon bulb 18. Light sources capable of being reliably strobed that produce a satisfactory spectrum of light can be used with the monitor 20 to measure the fiber sample 12 properties. As previously stated, a light source producing a white light is desirable because white light contains wavelengths ranging across the visible spectrum. Thus, visible features of the fiber sample 12 will tend to reflect some wavelength of the white light that can be detected.

The light pulse 16 produced by the Xenon bulb 18 is conducted by a light pipe 26 to a first photo sensitive diode 28. A preferred first photo sensitive diode 28 is preferably a blue enhanced silicon diode, model number SD290-12-22-241 manufactured by Advanced Photonix, Inc. of Camarillo Calif. The light pulse 16 also passes through the sample window 14 and is reflected by the fiber sample 12. This produces a reflected light pulse 34. The function of the light pipe 26 is to make the intensity of the light received by the first photo sensitive diode 28 generally independent of the degree to which the light pulse 16 is reflected by the fiber sample 12. The light pipe 26 conducts the light from the bulb 18 directly to the first photo sensitive diode 28. Thus, the intensity of the light pulse received by the first photo sensitive diode 28 directly from the light pipe 26 tends to be greater than the intensity of the light pulse 34 reflected back toward it. Therefore, the output of the first photo sensitive diode 28 tends to be unaffected by the intensity of the reflected light pulse 34. If the first photo sensitive diode 28 is not placed in the light pipe 26 with the Xenon bulb 18, then it may be greatly affected by the intensity of the light pulse 34. For example, suppose the fiber sample 12 was a very white and reflective piece of cotton and the first photo sensitive diode 28 was not placed in the light pipe 26. A white fiber sample 12 tends to reflect more light than a dark fiber sample 12. Because of the extra reflected light 34, the intensity of the light received by the first photo sensitive diode 28 would tend to be greater for a white fiber sample 12 than it would be when the fiber sample 12 was dark and not very reflective. Thus, the light pipe 26 tends to prevent the reflected light pulse 34 from appreciably affecting the output of the first photo sensitive diode 28.

In the preferred embodiment the light pipe 26 is a LEXAN block containing the first photo sensitive diode 28 and the Xenon bulb 18. However, the light pipe 26 may be formed of other light conducting materials such as glass, quartz, sapphire, or other appropriate thermoplastic resins. The function of the light pipe 28 is to insure that the light received by the first photo sensitive diode 28 is largely independent of the amount of light 34 reflected by the fiber sample 12. However, there are a variety of ways to perform this function that do not utilize a LEXAN block 26. For instance, the first photo sensitive diode 28 may be positioned so that it is physically shielded by the structure of the monitor 20 from most of the reflected light pulse 34.

The first photo sensitive diode 28 creates a voltage on signal line 50 representing the intensity of the light it receives. This voltage is received by processing means 30, which generates a synchronization signal when the voltage is at a desired level. In the preferred embodiment, the intensity of the light pulse 16 rises quickly to a variable maximum and then decays relatively slowly. At this light intensity the voltage produced by the first photo amplifier connected to the first photo sensitive diode 28 is between about 0 volts and about 8 volts.

When the intensity of the light pulse 16 received by the first photo sensitive diode 28 passes its peak intensity and falls to a value that is preferably about 80 percent of the typical maximum intensity first produced by a new bulb 18, the processing means 30 generates a synchronization signal. In the preferred embodiment, a voltage comparator and a voltage reference are used to determine when the 80 percent intensity value is reached. Preferably, the synchronization signal is generated when the voltage produced by the first photo amplifier connected to the first photo sensitive diode 28 is about 7 volts.

Every time the bulb 18 is strobed, the maximum intensity of the light 16 produced by it diminishes. Bulb life is measured by the time it takes the maximum intensity produced to degrade to a specified level, preferably about 80 percent of the typical maximum of a new bulb. The intensity value of 80 percent is preferred because it is the value typically used to measure bulb life. Thus, a good estimation of the bulb's 18 useful life in the monitor 20 may be obtained by referencing the bulb life provided by the manufacturer of the bulb 18.

However, if a longer useful bulb life is desired, the synchronization signal may be generated at a lower value, such as 50 percent of the original intensity of a new bulb. If a brighter light pulse 16 is desired, the synchronization signal can be generated at a higher value, such as 90 percent of the original intensity. However, operating at a brighter intensity results in a shorter useful life for the bulb 18. The synchronization signal is preferably generated when the light 16 is at an intensity that is high enough to allow the monitor 30 to receive enough reflected light 34 to function properly, as described more completely hereafter. Problems may arise if the synchronization signal is generated by the processing means 30 when the produced light pulse 16 reaches its maximum intensity. As the strobing bulb 18 degrades overtime, the maximum intensity produced decreases. Thus, the monitor 20 may need to be recalibrated.

The synchronization signal is generated on a negative edge of the light pulse 16 so that the readings will be taken at a more constant intensity. The negative edge of a light pulse is the trailing edge of the light pulse 16. This is where the intensity of the light 16 has passed its maximum and begun to fall. If the synchronization signal were generated as the intensity of the light pulse 16 increased, the intensity of the light pulse 16 might begin falling immediately after the synchronization signal was generated, or it might continue rising. This introduces an undesirable variable that may affect the intensity of the reflected light pulse 34 at the precise moment that the synchronization signal is generated.

Furthermore, in the preferred embodiment, the light pulse 16 rises to its maximum value relatively rapidly, between about 1 microseconds and about 3 microseconds, and then decays relatively slowly, between about 15 microseconds and about 50 microseconds. This means that the intensity of the light pulse 16 varies at a much slower rate on the negative edge of the light pulse 16. Thus, the intensity of the light pulse 16 will vary less during the time necessary for the first photo sensitive diode 28 to take a reading if the reading is taken on the negative edge. The monitor 20 tends to function better when the intensity of the reflected light pulse 34 depends primarily upon the properties of the fiber sample 12.

A second photo sensitive diode 32 receives the reflected light pulse 34 and is filtered to detect the intensity of that portion of the reflected light 34 having a wavelength of between about 500 nanometers and about 600 nanometers, and most preferably between about 505 nanometers and about 605 nanometers. A preferred second photo sensitive diode 32 is a blue enhanced silicon diode model number SD290-12-22-241 manufactured by Advanced Photonix, Inc. of Camarilio Calif. The second photo sensitive diode 32 sends a voltage signal on line 40 to the processing means 30. The voltage signal on line 40 is proportional to the intensity of the reflected light pulse 34 at the wavelengths described above. The processing means 30 captures the value of the voltage signal on line 40 at the moment that the synchronization signal is generated. Thus, the processing means 30 can determine the intensity of the reflected light pulse 34 at the given wavelengths at the precise moment that the intensity of the light pulse 16 is known. Thus, the intensity of the reflected light pulse 34 received by the second photo sensitive diode 32 will tend to be related to the reflective properties of the fiber sample 12 at those wavelengths, and not on the original intensity of the light pulse 16. This value is typically referred to as the reflection signal, which is representative of the reflectivity of the fiber sample 12. The reflectivity of cotton depends upon the lightness or darkness of the cotton fiber. This measurement is often referred to in the cotton industry as the grayness of the cotton.

A third photo sensitive diode 36 receives the reflected light pulse 34 and is filtered to detect the intensity of the light with a wavelength between about 530 nanometers and about 430 nanometers. A preferred third photo sensitive diode 36 is a blue enhanced silicon diode model number SD290-12-22-241 manufactured by Advanced Photonix, Inc. of Camarillo Calif. The third photo sensitive diode 36 sends a voltage signal on line 46 to the processing means 30. The voltage signal on line 46 is proportional to the intensity of the reflected light pulse 34 at the wavelengths described above. The processing means 30 captures the value of the voltage signal on line 46 at the moment that the synchronization signal is generated. Thus, the processing means 30 can determine the intensity of the reflected light pulse 34 at the given wavelengths at the precise moment that the intensity of the light pulse 16 is known. Thus, the intensity of the reflected light pulse 34 received by the third photo sensitive diode 36 tends to be related to the reflective properties of the fiber sample 12 at those wavelengths, and not on the original intensity of the light pulse 16. This value is typically referred to as the color signal, which is representative of the amount of yellow coloration of the fiber sample 12.

As discussed below, the various combinations of grayness and yellowness can be converted into color values by plotting the values on a official color chart provided by the United States Department of Agriculture. In the United States, cotton color grades fall into one of five color groups: White, Light Spotted, Spotted, Tinged and Yellow Stained. Cotton normally has a bright white color when it first opens. Thus, abnormal coloration generally indicates a deterioration in quality. It will be appreciated that, depending upon the type of fiber being monitored and the particular characteristics of the fiber that are to be measured, photo diodes that are sensitive to different wavelengths of light may be utilized. If premade photo sensitive diodes with the desired bandwidth cannot be obtained, filters can be used to restrict the wavelength of the reflected light 34 which reaches the photo sensitive diodes. Furthermore, it should be appreciated that the bandwidths given are approximate and that, as previously discussed, the monitor 20 is not strictly limited to devices which measure these wavelengths.

In addition to being received by the second photo sensitive diode 32 and the third photo sensitive diode 36, the reflected light pulse 34 is also received by a camera 38, such as a charge coupled device. A preferred camera 38 is model number V-1208 manufactured by Marshall. The charge coupled device camera 38 utilizes an array of light sensitive pixels to create an image of the fiber sample 12. The image consists of an array of light and dark pixels that is created by designating pixels receiving the reflected light pulse 34 at an intensity below a desired value as dark pixels and pixels receiving the reflected light pulse 34 at an intensity greater than the desired level as light pixels. The intensity of the light received by the charge coupled device camera 38 that qualifies a pixel as a light pixel can preferably be adjusted up or down. Thus, portions of the fiber sample 12 that are relatively less reflective, such as trash or leaves, create dark pixels in the image and portions of the fiber sample 12 that are relatively more reflective, such as white cotton fibers, create light pixels.

While the camera 38 of the preferred embodiment is a black and white camera, the camera 38 may be a color camera, or a series of black and white cameras fitted with filters so that color images of the fiber sample 12 are collected. For example, three single-chip charge coupled device arrays could each be fitted with a different filter so that each detected reflected light within different wavelength ranges. This may be accomplished with a red filter over one of the charge coupled device arrays, a blue filter over a second of the charge coupled device arrays, and a green filter over a third of the charge coupled device arrays. The red filter is preferably tuned to wavelengths of between about 600 nanometers and about 700 nanometers, the green filter to wavelengths of between about 500 and about 600 nanometers, and the blue filter to wavelengths of between about 400 and about 500 nanometers. Preferably, a 0.3 neutral density filter is used in conjunction with the red filter, and a 0.5 neutral density filter is used in conjunction with the green filter.

In yet a further alternate embodiment, instead of having three charge coupled device arrays, each with its own filter, a single charge coupled device array is used, and the three filters are placed above the array one at a time and three different images are acquired. Then, the three images may either be formed into a single composite image, or analyzed by the processing means 30 separately. Further, a prism can be used to break the reflected light into it wavelength components, with different wavelengths focused onto different portions of the charge coupled array. In this manner, the relative intensity of the reflected light at many different wavelengths may be detected and subsequently analyzed.

When the camera 38 is a color camera, the information provided by the second photosensitive diode 32 and third photosensitive diode 36 may be provided by the camera 38, and the diodes 32 and 36 are not required. By receiving the color information from the camera 38 instead of the diodes 32 and 36, many more readings are taken on the sample 12. In other words, instead of just two single point measurements, one measurement by each of the diodes 32 and 36, a number of readings equal to the number of pixels in the array of the camera 38 are taken on each fiber sample 12. Thus, a color distribution for the fiber sample 12 can be quickly acquired and determined. This information provides more insight into the range of colors within the fiber sample 12, than does the averaged reading provided by the diodes 32 and 36. Thus, the camera 38 may provide the reflectance and color signals described above.

The output of the charge coupled device camera 38 is sent to the processing means 30 on a signal line 42. If the fiber being monitored is cotton, this output represents the leaf and trash content of the fiber sample 12. In the cotton ginning industry, leaf material is considered waste and there is an additional cost factor associated with its removal. Thus, it is important for purchasers and sellers of cotton to be able to determine the leaf content of the cotton fiber. One function of the charge coupled device camera 38 is to capture images of the fiber sample 12 so that the processing means 30 can determine the trash content represented in the image.

By examining the color, fuzziness, shape, and size of the defects detected in the images created by the camera 38, the processing means 30 preferably determines the types of impurity or defects in the fiber sample 12. For example, a nep may appear white, or in other words, have a stronger reflectance in certain wavelengths, while a piece of bark will appear darker or brown, and have a reduced reflectance in certain wavelengths. Further, a piece of leaf will appear green, and have reflectance characteristics associated with its color as well. Thus, the color information, or in other words the spectral information, received by the camera 38 can be used by the processing means 30 to classify different types of trash in the fiber sample 12.

Likewise, the fuzziness of the defects, or patterns of dark pixels in the image, tends to indicate the type of impurity detected. Fuzziness refers to the rate of change in the darkness of the pixels across a cross section of the pattern. In other words, some impurities have sharp edges and create a rapid change in the amount of light that passes through them. A piece of leaf is a good example of this type of impurity. At the edge of the leaf, the gray level of the image undergoes a dramatic change. Just to the outside of the edge of the leaf, the gray level is at some base level, and just to the inside of the edge of the leaf the gray level is at a dramatically darker level.

Other types of impurities tend to produce a more gradual change in the amount of light that is transmitted. For example, a nep typically does not have an edge profile similar to the leaf described above. A nep tends to have a relatively more dense core surrounded by a relatively less dense periphery. Thus, the change in the amount of light transmitted just outside of the edge of the nep and just inside of the edge of the nep is not very great in comparison to the change at the edge of a leaf. However, unlike the profile of the leaf, the amount of light transmitted continues to change across the profile of the nep, moving from the edge of the nep to the center of the nep. Typically, the center of the nep will be the darkest area of the nep, and the amount of light transmitted will gradually increase in all directions away from the center of nep.

Preferably, the shape of the detected pattern is also used by the processing means 30 to help classify the pattern or impurity. Entanglement neps, seed coat neps, leaves, twigs, and other impurities all tend to have distinctive shapes. The processing means determines a shape profile for the impurity that has been detected, and uses the determined shape to help classify the impurity. Shape can be determined with methods that approximate the peripheral edge of the impurity with simple geometric figures. Alternately, another method for determining the shape of an impurity is to represent the shape or peripheral path of the impurity with moments or center of gravity. This method works well when classifying impurities that are not irregular in shape, but are more nearly circular. In the preferred embodiment, more than one pattern recognition method is used to help classify the impurity.

For example, twigs tend to have a relatively high aspect ratio. In other words, one dimension of a twig, such as length, tends to be much greater than another dimension of the twig, such as width. Conversely, neps tend to have a relatively low aspect ratio, meaning that the measurements of a nep tend to be more equal in all directions. The processing means 30 analyzes the detected pattern and determines the aspect ratio, such as by counting the number of pixels used to represent the pattern along two different axis. Irregular shapes, or in other words, shapes than are not generally circular or generally rectangular, may be indicative of a leaf fragment. Thus, the shape of the detected pattern is preferably used by the processing means 30 to help classify the impurity.

Size may also be used to classify impurities in the sliver of cotton fiber. For example, a specific gin may find that trash in its feed stream tends to be larger than the neps. Thus, the processing means 30 can be programmed such that a detected pattern over a given size is used as an indication that the impurity is trash and not a nep. Thus, the size is preferably used to help classify the impurity.

The color, fuzziness, shape, and size data can be used by the processing means 30 in different ways. The levels or values assigned to each of the criteria can be put into an equation to classify the impurity. Alternately, the levels are compared by the processing means 30 to a classifier to determine what type of impurity is represented. The classifier contains color, fuzziness, shape, and size data from known types of impurities. If the color, fuzziness, shape, and size data calculated by the processing means 30 closely corresponds to the data for a known impurity, the pattern of dark pixels is classified as that type of impurity. This information can be fed backward or forward to control fiber processing equipment to reduce or eliminate the impurity. For example, additional cleaners may be used to further clean a cotton feed stream in a gin, when the processing means 30 indicates that an excessive amount of trash is remaining in the lint.

It should be appreciated that the current invention is not limited to a device with a charge coupled device camera 38. The charge coupled device camera 38 is the photo sensitive device of the preferred embodiment that is used to obtain an image of the cotton sample 12. The resolution of the camera 18 chosen depends upon the size of the particles desired to be detected. Using more pixels to represent a sample of the same size will allow smaller particles of trash to be detected. Using less pixels to represent the fiber sample 12, allows only relatively large particles to be detected. The preferred array size is about 512 pixels by about 480 pixels. Thus, many different types of photo sensitive detection devices could be used to receive the reflected light pulse 34 without departing from the spirit of the invention. The processing means 30 captures the image data on line 42 at the moment that the synchronization signal is generated. Thus, the reflection signal on line 40, the color signal on line 46, and the image data on line 42 are all captured at the same moment.

Preferably, the second photo sensitive diode 32, the third photo sensitive diode 36, and the charge coupled device camera 38 receive the light reflected through the entire sample window 14. The preferred embodiment uses a prism 25 to focus the reflected light pulse 34 from the entire sample window 14 upon the photo sensitive detection devices. However, it should be recognized that there are alternate ways in which the invention could be constructed. For example, the second photo sensitive diode 32 and the third photo sensitive diode 36 could be located beneath their own respective sample windows 14. The advantage of using the prism 25 is that all of the photo sensitive devices take readings based upon the light reflected from the same fiber sample 12. However, if the fiber is of uniform quality, this feature may not be as important.

Depending upon the level of accuracy required, two sources of drift or calibration change that may need to be taken into account are the changing temperature inside the monitor 20 or the possibility of contamination on the glass of the sample window 14. Temperature changes can affect the sensitivity of electronic components such as a photosensitive diode. Thus, fluctuations in temperature will cause fluctuations in the measurements taken by the monitor 20 even if the properties of the fiber sample 12 remain unchanged. As previously discussed, this is undesirable. The temperature can be kept at a constant value by using heaters to warm the electrical components of the monitor 20. A preferred heater is a model number P5504A050Z150A manufactured by Advanced Thermal Products, Inc. In the preferred embodiment, the heaters are set to about 50 degrees C. This allows for the normal heat build-up within the enclosures themselves plus the added ambient temperature.

Similarly, if a piece of dirt is stuck on the sample window 14, the monitor 20 may interpret it as a piece of trash in every fiber sample 12. In order to avoid contamination of the glass, the sample window 14 can be fitted with a wiper to clear away any fiber that is stuck to the window 14. Similarly, the sample window 14 can be positioned so that excess fiber does not come to rest upon the sample window 14 when the monitor 20 is in operation. Alternatively, the sample window 14 may be manually inspected and washed at regular intervals. In a somewhat different approach, the processing means 30 could be programed to recognize a reoccurring pattern in the array of pixels as a piece of trash stuck to the sample window 14 and compensate for it accordingly. For example, a tare frame, or reference frame, of the window is generated by the camera 38, and this tare frame is electronically subtracted from all subsequent sample frames. Alternately, a tare frame can be generated just prior to each sample frame.

Once measurements of the fiber sample 12 have been taken by the aforementioned photo sensitive detection devices, they are then analyzed by the processing means 30. The processing means 30 may be a simple microprocessor or an entire computer. Preferably, the processing means 30 includes an input/output for receiving and sending signals on the lines 21, 24, 40, 42, 46, 48, and 50, an analog to digital converter, memory for storing data and processing instructions, and a microprocessor for processing data and instructions. Other items such as a user interface and a display may also be included in the processing means 30. As will be discussed in more detail, the sophistication of the processing means 30 used to analyze the output of the aforementioned photo sensitive detectors depends upon the complexity of the functions to be performed.

The color signal and the reflection signal received by the processing means 30 on lines 40 and 46 are analyzed by the processing means 30 to produce a composite value. This composite value represents the color grade of the fiber sample 12 being monitored. The processing means 30 also produces a percentage value representing the percentage of dark pixels in the array of dark and light pixels. This value represents the leaf and trash content of the fiber sample 12 being monitored. Furthermore, the processing means 30 may recognize and classify patterns of dark pixels in the array of light and dark pixels. Certain patterns will tend to represent leaves or other extraneous matter in the fiber sample 12. Depending upon the sophistication of the processing means 30 utilized and the particular needs and concerns of the user, the output signals of the photo detection devices may be manipulated in a variety of ways to obtain useful information about the fiber sample 12.

The voltage measurements received by the processing means 30 are not yet in the same form as measurements taken by a human classer. However, the processing means 30 preferably has the ability to adjust the measurements into the same form, or any other form desired. As briefly discussed above, human classers rely on their senses to grade cotton. Thus, the grades assigned to cotton by a human classer are subjective, and vary by classer, and even from moment to moment by the same classer. This introduces some undesirable variability into the grading of cotton. However, the monitor of the present invention is able to make these measurements in a repeatable fashion, and thus have the capability to replace classing by human.

Cotton is typically classed using a three digit code that ranges from 11-1 to 85-5. The first digit represents the reflectance of the cotton. This first digit varies in value from 1 to 8. The lower the number, the more reflective the cotton. A value of 8 represents subgrade cotton. The second digit varies from 1 to 5 and represents the color of the cotton. A 1 in the second position represents a whiter cotton sample while a 4 designates a yellower cotton sample. A value of 5 represents subgrade cotton. The third digit further divides the class designated by the first two digits into subclasses according to the trash content and quality of the cotton. The best cotton in the class is designated with a 1 while the worst is designated with a 4. A value of 5 represents subgrade cotton.

In the monitor 20, the second photo sensitive diode's 32 output is received by the processing means 30 as a voltage. However, the reflectance of cotton is generally measured in terms of a value known as Rd. Normally, cotton has an Rd value of between about 48 and about 82. The higher the Rd value, the whiter and more reflective the cotton. The third photo sensitive diode's 36 output is also received as a voltage by the processing means 30. However, the color of cotton is generally measured in terms of a +b value. Normally, cotton has a +b value of between about 5.0 and about 17.0. The higher the +b value, the yellower the cotton. Therefore, the voltage measurements received from the second and third photo sensitive diodes 32 and 36 are converted into Rd and +b values by the processing means 30.

In addition to manipulating the output voltages of the photo sensitive diodes, the processing means 30 also manipulates the output of the charge coupled device camera 38. For example, the processing means 30 analyzes the array of light and dark pixels and calculates a value representing the percentage of dark pixels in the array. This percentage value is used to represent the trash or leaf content of the cotton fiber.

The monitor is calibrated to provide readings using the traditional cotton classifications described above. Colored tile calibration samples representing known classifications are placed in front of the sample window 14. The outputs of the photo sensitive devices 32, 36 and 38 are then manipulated until the outputs of the monitor 20 correspond to the known values for the calibration samples. The calibration of the monitor 20 can then be rechecked whenever desired by placing the calibration samples on the sample window 14 and confirming that the readings provided by the monitor 20 are the same as those for the known samples. The monitor 20 is then ready to read a cotton sample.

Figure 3:
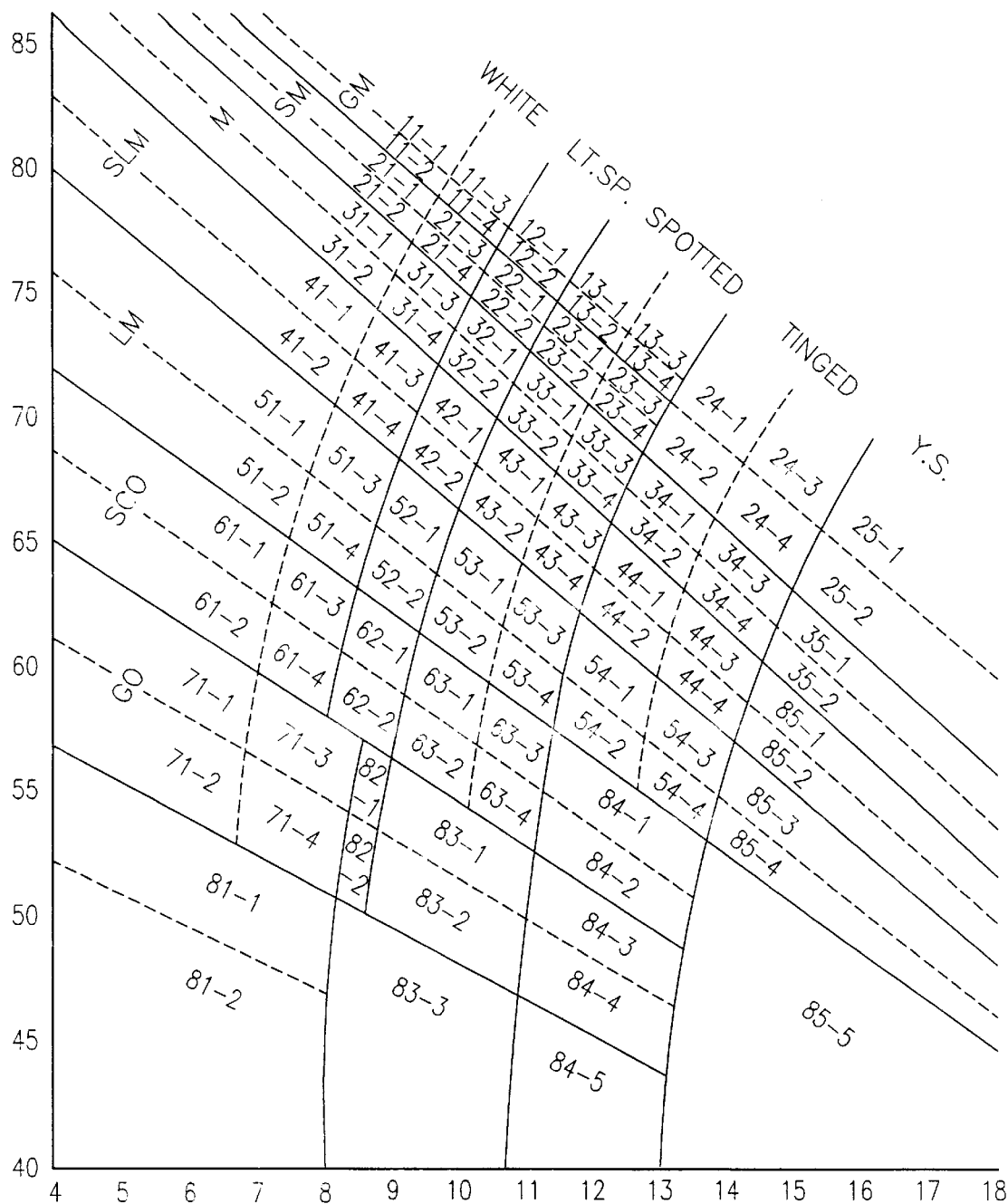
FIG. 3 is an official cotton color chart for American upland cotton from the USDA, Agricultural Marketing Service, Cotton Division.

For an example, a particular cotton sample may produce voltage levels that correspond to an Rd of 74 and a +b value of 10.0, and the array of light and dark pixels may have 0.20 percent dark pixels. By comparing these values to an internal version of the chart graphically depicted in FIG. 3, the processing means 30 designates a grade of 32-1 for the cotton fiber sample, and presents this value, such as on a display. The reflectance value of 3 represents a light grade of cotton referred to as Middling cotton. The color value of 2 further classifies the cotton sample as Light Spotted cotton. Thus, the fiber sample is classed as Light Spotted Middling cotton. The percentage value of 0.20 is used to classify the trash content of the fiber sample. If desired, it can be converted to one of the seven leaf grades historically used by human classers by comparing it to a table that contains the percentage of trash typically contained in each of the leaf grades. The third digit of 1 designates the sample as the highest grade of Light Spotted Middling cotton, meaning that it has a very low trash content.

Figure 2:
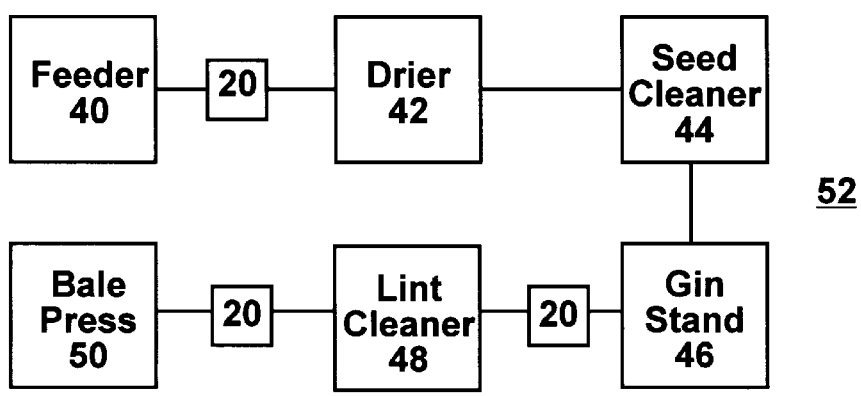
FIG. 2 is a functional representation of a cotton gin showing some possible locations for monitors in a cotton gin.

Referring to FIG. 2, in a typical cotton ginning operation, the monitor 20 may be used to adjust the fiber processing equipment in response to changes in the measured properties of the fiber sample 12. For example, in a cotton gin 52, the monitor 20 could be positioned after the feeder 40. As the cotton is initially fed into the cotton gin, a monitor 20 is activated approximately every five to six seconds to determine the starting quality of the cotton fiber. The activation period of the monitor 20 can be manipulated according to the expected rate of change in the properties of the fiber sample 12. These initial quality readings can be used to manipulate the functioning of the cotton gin 52. If the cotton is relatively clean, the time spent by the cotton being processed in certain portions of the cotton gin 52 may be cut short. If the cotton is relatively dirty, the time spent being processed may be increased.

After the initial monitor 20 reading, the cotton fiber would then proceed to a drier 42 and a seed cleaner 44. From there, the cotton is taken into a gin stand 46. Upon leaving the gin stand 46, the cotton fiber is once more monitored by the monitor 20 to determine if the seed cleaner 44 and gin stand 46 are functioning properly. If they are not, the operation of the seed cleaner 44 and the gin stand 46 machines can be modified to improve their performance or the cotton can be returned to the gin stand 46 and seed cleaner 44 and repeat the process again. Finally, the cotton goes through a lint cleaner 48 and passes another monitor 20 before being made into bales by a bale press 50. This final reading can be used to determine if the entire system is functioning properly. If the system needs adjustment, the measurements taken can be fed back to the processing equipment to alter the system's functioning accordingly. Additionally, the results of the final measurements may be stamped on the bale of cotton to designate its quality.

While specific embodiments of the invention have been described with particularity above, it will be appreciated that the invention comprehends rearrangement and substitution of parts within the spirit of the appended claims.

What is claimed is:

1. A fiber quality monitoring device comprising:

a sample window for viewing a fiber sample, a strobing light source for providing a light pulse that is directed toward and reflected by the fiber sample, a first photo sensitive detector for detecting when the light pulse directed toward the fiber sample reaches a desired intensity, and generating a synchronization signal when the light pulse directed toward the fiber sample reaches the desired intensity, and a second photo sensitive detector positioned to receive the reflected light pulse for measuring properties of the fiber sample when the synchronization signal is generated.

2. The device of claim 1 wherein the synchronization signal is generated on a negative edge of the light pulse produced by the strobing light source.

3. The device of claim 1 wherein the strobing light source comprises a Xenon bulb.

4. The device of claim 1 wherein the second photo sensitive detector comprises a photo diode for detecting light with a wavelength between about 500 nanometers and about 600 nanometers.

5. The device of claim 1 wherein the second photo sensitive detector comprises a photo diode for detecting light with a wavelength between about 430 nanometers and about 530 nanometers.

6. The device of claim 1 wherein the second photo sensitive detector comprises two photo diodes and a camera.

7. The device of claim 1 wherein the second photo sensitive detector comprises a charge coupled device camera having an array of pixels for generating an array of values representing properties of the fiber sample.

8. The device of claim 7 further comprising processing means for recognizing and classifying patterns of values in the generated array of values.

9. The device of claim 8 further comprising processing means for controlling fiber processing equipment in response to the patterns of values classified in the generated array of values.

10. The device of claim 1 further comprising processing means for analyzing the fiber sample properties measured by the second photo sensitive detector.

11. A fiber quality monitoring device comprising:

a sample window for viewing a fiber sample, a strobing Xenon bulb for providing a light pulse that is directed toward and reflected by the fiber sample, a first photo diode for generating a synchronization signal on a negative edge of the light pulse when the light pulse reaches a desired intensity, a second photo diode positioned to receive the reflected light pulse for detecting light with a wavelength between about 500 nanometers and about 600 nanometers and for producing a reflection signal in synchronization with the synchronization signal, a third photo diode positioned to receive the reflected light pulse for detecting light with a wavelength between about 430 nanometers and about 530 nanometers and producing a color signal in synchronization with the synchronization signal, a charge coupled device camera positioned to receive the reflected light pulse and having an array of pixels for creating an array of light and dark pixels by designating pixels receiving the reflected light pulse at an intensity below a desired value as dark pixels and pixels receiving the reflected light pulse at an intensity greater than the desired level as light pixels, a prism for focusing the reflected light pulse received by the second and third photo diodes, a transparent block enclosing the first photo diode and the strobing Xenon bulb for conducting the light pulse from the Xenon bulb to the first photo diode, and processing means for:
analyzing the color signal and the reflection signal and for producing a composite value,
producing a percentage value representing the percentage of dark pixels in the array of dark and light pixels,
recognizing and classifying patterns of dark pixels in the array of light and dark pixels, and
controlling fiber processing equipment in response to the classified patterns.

12. The device of claim 11 further comprising a paddle that captures the fiber sample from a stream of air entrained fiber for placing the fiber sample on the sample window.

13. The device of claim 11 wherein the fiber sample further comprises a fiber batt sliding past the sample window.

14. The device of claim 11 wherein the fiber sample further comprises air entrained fiber flowing past the sample window in a stream.

15. A monitoring device for controlling a cotton gin comprising:

a sample window for viewing a cotton sample, a strobing light source for providing a light pulse that is directed toward and reflected by the cotton sample, thereby producing a reflected light pulse, a charge coupled device camera positioned to receive the reflected light pulse, and having an array of pixels for creating an array of light and dark pixels by designating pixels receiving the reflected light pulse at an intensity below a desired value as dark pixels and pixels receiving the reflected light pulse at an intensity greater than the desired level as light pixels, and processing means for:
recognizing and classifying patterns of dark pixels in the array of light and dark pixels,
associating the recognized and classified patterns with known types of trash, and
controlling the cotton gin in response to the types of trash detected in the cotton sample.

16. A monitoring device for controlling a cotton gin comprising:

a sample window for viewing a cotton sample, a strobing Xenon bulb for providing a light pulse that is directed toward and reflected by the cotton sample, a first photo diode for generating a synchronization signal on a negative edge of the light pulse when the light pulse reaches a desired intensity, a second photo diode positioned to receive the reflected light pulse for detecting light with a wavelength between about 500 nanometers and about 600 nanometers and for producing a reflection signal in synchronization with the synchronization signal, a third photo diode positioned to receive the reflected light pulse for detecting light with a wavelength between about 430 nanometers and about 530 nanometers and producing a color signal in synchronization with the synchronization signal, a charge coupled device camera positioned to receive the reflected light pulse and having an array of pixels for creating an array of light and dark pixels by designating pixels receiving the reflected light pulse at an intensity below a desired value as dark pixels and pixels receiving the reflected light pulse at an intensity greater than the desired level as light pixels, a prism for focusing the reflected light pulse received by the second and third photo diodes, a transparent block enclosing the first photo diode and the strobing Xenon bulb for conducting the light pulse from the Xenon bulb to the first photo diode, and processing means for:
analyzing the color signal and the reflection signal and for producing a composite value,
producing a percentage value representing the percentage of dark pixels in the array of dark and light pixels,
recognizing and classifying patterns of dark pixels in the array of light and dark pixels, and
controlling the cotton gin in response to the classified patterns.

17. A cotton gin subsystem comprising:

an input for receiving cotton, a cleaner for cleaning the cotton, an output for providing cleaned cotton, conduits for transporting the cotton between the input, cleaner, and output, a sample window disposed within at least one of the conduits, for viewing a moving sample of the cotton, a strobing light source for providing a light pulse that is directed toward and reflected by the cotton sample, a charge coupled device camera positioned to receive the reflected light pulse and having an array of pixels for detecting impurities within the sample of cotton, producing a color signal, and producing a reflection signal, processing means for:
analyzing the color signal and the reflection signal and for producing a composite value,
recognizing and classifying patterns of the impurities, and
controlling at least one of the input, cleaner, and output in response to the classified patterns.

18. A method for detecting fiber sample properties comprising:

viewing a fiber sample through a sample window, strobing a light source to produce a light pulse that is directed toward and reflected by the fiber sample, detecting an intensity of the light pulse directed toward the fiber sample, generating a synchronization signal when the intensity of the light pulse directed toward the fiber sample reaches a desired intensity, detecting an intensity of the reflected light pulse at a wavelength when the synchronization signal is generated, the intensity of the reflected light pulse at the wavelength being representative of the properties of the fiber sample.

19. The method of claim 18 wherein the step of generating a synchronization signal further comprises generating the synchronization signal on a negative edge of the light pulse produced by the strobing light source.

20. The method of claim 18 wherein the step of detecting an intensity of the reflected light pulse further comprises detecting an intensity of the reflected light pulse at a wavelength between about 500 nanometers and about 600 nanometers.

21. The method of claim 18 wherein the step of detecting an intensity of the reflected light pulse further comprises detecting an intensity of the reflected light pulse at a wavelength between about 430 nanometers and about 530 nanometers.

22. The method of claim 18 further comprising the step of generating an array of values representing the properties of the fiber sample.

23. The method of claim 22 further comprising the step of recognizing and classifying patterns of values in the generated array of values.

24. The method of claim 23 further comprising the step of controlling subsequent processing of the fiber sample in response to the classified patterns of values in the generated array of values.

25. The method of claim 18 further comprising the step of analyzing the detected intensity of the reflected light pulse at the wavelength to determine the properties of the fiber sample.

26. A method for determining fiber sample properties comprising:

viewing a fiber sample through a sample window, strobing a Xenon bulb to produce a light pulse that is directed toward and reflected by the fiber sample, generating a synchronization signal on a negative edge of the light pulse when the light pulse reaches a desired intensity, focusing the reflected light pulse, detecting a first intensity of the reflected light pulse at a wavelength between about 500 nanometers and about 600 nanometers, producing a reflection signal based on the first intensity in synchronization with the synchronization signal, detecting a second intensity of the reflected light pulse at a wavelength between about 430 nanometers and about 530 nanometers, producing a color signal based on the second intensity in synchronization with the synchronization signal, receiving the reflected light pulse with pixels and creating an array of light and dark pixels by designating each pixel receiving the reflected light pulse at an intensity below a desired value as a dark pixel and designating each pixel receiving the reflected light pulse at an intensity greater than the desired value as a light pixel, analyzing the color signal and the reflection signal to produce a composite value, producing a percentage value representing the percentage of dark pixels in the array of dark and light pixels, recognizing and classifying patterns of dark pixels in the array of light and dark pixels, and controlling fiber processing equipment in response to the classified patterns.

27. A method for determining fiber sample properties comprising:

viewing a fiber sample through a sample window by capturing the fiber sample from a stream of air entrained fiber and placing the fiber sample on the sample window, strobing a Xenon bulb to produce a light pulse that is directed toward and reflected by the fiber sample, generating a synchronization signal on a negative edge of the light pulse when the light pulse reaches a desired intensity, focusing the reflected light pulse, detecting a first intensity of the reflected light pulse at a wavelength between about 500 nanometers and about 600 nanometers, producing a reflection signal based on the first intensity in synchronization with the synchronization signal, detecting a second intensity of the reflected light pulse at a wavelength between about 430 nanometers and about 530 nanometers, producing a color signal based on the second intensity in synchronization with the synchronization signal, receiving the reflected light pulse with pixels and creating an array of light and dark pixels by designating each pixel receiving the reflected light pulse at an intensity below a desired value as a dark pixel and designating each pixel receiving the reflected light pulse at an intensity greater than the desired value as a light pixel, producing a percentage value representing the percentage of dark pixels in the array of dark and light pixels, recognizing and classifying patterns of dark pixels in the array of light and dark pixels, and controlling fiber processing equipment in response to the classified patterns.

28. A method for determining fiber sample properties comprising:

viewing a fiber sample through a sample window by sliding the fiber sample in the form of a fiber batt past the sample window, strobing a Xenon bulb to produce a light pulse that is directed toward and reflected by the fiber sample, generating a synchronization signal on a negative edge of the light pulse when the light pulse reaches a desired intensity, focusing the reflected light pulse, detecting a first intensity of the reflected light pulse at a wavelength between about 500 nanometers and about 600 nanometers, producing a reflection signal based on the first intensity in synchronization with the synchronization signal, detecting a second intensity of the reflected light pulse at a wavelength between about 430 nanometers and about 530 nanometers, producing a color signal based on the second intensity in synchronization with the synchronization signal, receiving the reflected light pulse with pixels and creating an array of light and dark pixels by designating each pixel receiving the reflected light pulse at an intensity below a desired value as a dark pixel and designating each pixel receiving the reflected light pulse at an intensity greater than the desired value as a light pixel, producing a percentage value representing the percentage of dark pixels in the array of dark and light pixels, recognizing and classifying patterns of dark pixels in the array of light and dark pixels, and controlling fiber processing equipment in response to the classified patterns.

29. A method for determining fiber sample properties comprising:

viewing a fiber sample through a sample window by passing the fiber sample in the form of air entrained fiber in a stream past the sample window, strobing a Xenon bulb to produce a light pulse that is directed toward and reflected by the fiber sample, generating a synchronization signal on a negative edge of the light pulse when the light pulse reaches a desired intensity, focusing the reflected light pulse, detecting a first intensity of the reflected light pulse at a wavelength between about 500 nanometers and about 600 nanometers, producing a reflection signal based on the first intensity in synchronization with the synchronization signal, detecting a second intensity of the reflected light pulse at a wavelength between about 430 nanometers and about 530 nanometers, producing a color signal based on the second intensity in synchronization with the synchronization signal, receiving the reflected light pulse with pixels and creating an array of light and dark pixels by designating each pixel receiving the reflected light pulse at an intensity below a desired value as a dark pixel and designating each pixel receiving the reflected light pulse at an intensity greater than the desired value as a light pixel, producing a percentage value representing the percentage of dark pixels in the array of dark and light pixels, recognizing and classifying patterns of dark pixels in the array of light and dark pixels, and controlling fiber processing equipment in response to the classified patterns.

* * * * *